US012724027B2

(12) United States Patent
Nakajima et al.

(10) Patent No.: US 12,724,027 B2
(45) Date of Patent: Sep. 1, 2026

(54) IMMUNOCHROMATOGRAPHIC TEST STRIP

(71) Applicant: SEKISUI MEDICAL CO., LTD., Tokyo (JP)

(72) Inventors: Akira Nakajima, Tokyo (JP); Kanako Itou, Tokyo (JP); Keigo Kohno, Tokyo (JP); Shun Sakai, Tokyo (JP); Motoki Morita, Tokyo (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 0 days.

(21) Appl. No.: 17/285,046

(22) PCT Filed: Oct. 21, 2019

(86) PCT No.: PCT/JP2019/041281

§ 371 (c)(1),
(2) Date: Apr. 16, 2024

(87) PCT Pub. No.: WO2020/085289

PCT Pub. Date: Apr. 30, 2020

(65) Prior Publication Data

US 2021/0293806 A1 Sep. 23, 2021

(30) Foreign Application Priority Data

Oct. 23, 2018 (JP) ................................ 2018-198883

(51) Int. Cl.
*G01N 33/543* (2006.01)
*G01N 33/53* (2006.01)

(52) U.S. Cl.
CPC ... *G01N 33/54386* (2013.01); *G01N 33/5306* (2013.01)

(58) Field of Classification Search
CPC ......... G01N 33/54386; G01N 33/5306; G01N 33/54387; G01N 33/54388; G01N 33/54389; G01N 33/54391
USPC .......................................................... 436/501
See application file for complete search history.

(56) References Cited

U.S. PATENT DOCUMENTS

| | | | |
|---|---|---|---|
| 9,863,945 B2 | 1/2018 | Ito | |
| 2013/0162981 A1* | 6/2013 | Emeric | G01N 33/48785 204/403.03 |
| 2014/0093865 A1 | 4/2014 | Espinosa et al. | |
| 2015/0118675 A1* | 4/2015 | Ito | G01N 33/538 435/5 |
| 2016/0223571 A1 | 8/2016 | Pieribone | |
| 2017/0131274 A1 | 5/2017 | Suzuki et al. | |
| 2017/0191996 A1 | 7/2017 | Johnson et al. | |
| 2019/0064160 A1 | 2/2019 | Okuyama et al. | |

FOREIGN PATENT DOCUMENTS

| | | | |
|---|---|---|---|
| EP | 3 153 858 A1 | | 4/2017 |
| EP | 3 407 065 A1 | | 11/2018 |
| JP | 11-153600 A | | 6/1999 |
| JP | H11153600 A | * | 6/1999 |
| JP | 2002-82117 A | | 3/2002 |
| JP | 2013-195403 A | | 9/2013 |
| JP | 2015-1395 A | | 1/2015 |
| JP | 2015-230221 A | | 12/2015 |
| JP | 2017-129533 A | | 7/2017 |
| JP | 2018-25426 A | | 2/2018 |
| WO | WO 2015/186812 A1 | | 12/2015 |
| WO | WO 2017/126593 A1 | | 7/2017 |
| WO | WO 2018/030365 A1 | | 2/2018 |
| WO | WO 2018/060706 A1 | * | 4/2018 |

OTHER PUBLICATIONS

BeMiller et al., Carbohydrate Chemistry for Food Scientists (3rd Edition), 2019, Chapter 1, Monosaccharides, Elsevier, p. 18, second paragraph,. Retrieved from https://app.knovel.com/hotlink/pdf/id:kt011Y7Z22/carbohydrate-chemistry/monosaccharides on Jul. 29, 2025. (Year: 2019).*
Japanese Office Action for Japanese Application No. 2020-553384, dated May 10, 2023, with an English translation.
International Preliminary Report on Patentability and English translation of the Written Opinion of the International Searching Authority, dated May 6, 2021, for International Application No. PCT/JP2019/041281.
International Search Report, issued in PCT/JP2019/041281, dated Dec. 24, 2019.
Paek et al., "Development of Rapid One-Step Immunochromatographic Assay", Methods, 2000, vol. 22, pp. 53-60.
Written Opininon of the International Searching Authority, issued in PCT/JP2019/041281, dated Dec. 24, 2019.
Extended European Search Report for corresponding European Application No. 19875645.4, dated Jun. 27, 2022.
Chinese Office Action and Search Report for Chinese Application No. 201980068191.6, dated Mar. 1, 2024, with an English translation.

* cited by examiner

*Primary Examiner* — Gregory S Emch
*Assistant Examiner* — Omar Ramadan
(74) *Attorney, Agent, or Firm* — Birch, Stewart, Kolasch & Birch, LLP

(57) ABSTRACT

The present invention provides an immunochromatographic test strip capable of avoiding so-called blank color development in an immunochromatographic test strip and enabling more accurate determination.

The present invention provides an immunochromatographic test strip comprising at least a sample application region, a development region, and a detection region in which an antibody is immobilized, wherein the detection region includes the antibody and one or more saccharides selected from the group consisting of a reductive monosaccharide and a reductive disaccharide.

13 Claims, 2 Drawing Sheets

IMMUNOCHROMATOGRAPHIC TEST STRIP

TECHNICAL FIELD

The present invention relates to a test strip for immunochromatography and an immunochromatographic detection method using the test strip.

BACKGROUND ART

As use of POCT (point of care testing) for treatment near patients becomes widespread, a lateral flow immunochromatographic detection method using a test strip of nitrocellulose membrane etc. becomes widely used as a simple immunoassay using antigen-antibody reaction.

An immunochromatography based test strip (hereinafter referred to as an immunochromatographic test strip) generally consists of a sample application region, a development region, and a detection region located on a porous membrane. A labeled antibody targeting a specific analyte is held in the development region so as to be able to travel down the development region and reach the detection region, by dissolving upon contact with a specimen (sample). An antibody responsible for analyte detection is immobilized in a certain spot on the development region to constitute the detection region. When the specimen is dropped onto the sample application region, and the specimen includes an analyte, the analyte specifically binds to the labeled antibody to form a complex. The complex is developed in the development region in the downstream direction and binds to the immobilized antibody in the detection region. In this way, a sandwich-type complex of the labeled antibody, the analyte, and the immobilized antibody is formed in the detection region, and therefore, the analyte can qualitatively or quantitatively be analyzed by detecting a signal derived from a label.

A conventional immunochromatographic detection method has problems of background binding and blank color development of immunochromatographic test strips. The background binding means that a site other than the detection region in the membrane is colored, and it is considered to be due to a hydrophobic binding of the labeled antibody to the membrane. The blank color development means that the detection region develops color when the blank sample in which a detection substance does not exist is measured, and is also referred to as non-specific color development since this is a non-specific reaction. The blank color development is considered to be problematic because it causes a false positive giving an incorrect determination result in the case of visual determination, and it causes deterioration in detection sensitivity, i.e., detectability of a specific signal, in the case of determination by an optical device.

To achieve a reduction of the blank color development, Patent Document 1 discloses an immunochromatographic apparatus in which a labeling substance is protected with polyalkylene glycol having one or more mercapto groups having a molecular weight of 2000 to 20000 etc. so as to stabilize the labeling substance in drying and holding and then dried and held together with arginine and casein in a labeling substance holding part. It is also described that fructose is included as a protective stabilizing substance or a dissolution promoting substance in a labeling substance solution (paragraph 0032).

Patent Document 2 describes that when a labeling substance is held in a liquid form or a dry state, saccharide is included together in the kit. Although the purpose of allowing saccharide to coexist is not clear, it is presumed that this is performed for stabilizing labeling substances such as latex particles as in Patent Document 1.

In addition, methods of adding a protein or a surfactant to suppress blank color development have been adopted; however, even if blank color development is suppressed, detection sensitivity of an analyte is also reduced at the same time, these measures are still not sufficient. Additionally, if the labeling substance is modified with a functional group etc. as in Patent Document 1, new problems such as contamination of impurities may occur.

CITATION LIST

Patent Literature

Patent Document 1: Japanese Laid-Open Patent Publication No. 2013-195403

Patent Document 2: Japanese Laid-Open Patent Publication No. 2002-082117

SUMMARY OF INVENTION

Technical Problem

From the above, a problem still exists in terms of reducing blank color development while maintaining sufficient detection sensitivity for an analyte without contaminating impurities. A problem to be solved by the present invention is to provide an immunochromatographic test strip suppressing so-called blank color development in the immunochromatographic test strip by an approach different from the prior arts, avoiding false positives to prevent incorrect determination, and capable of achieving higher detection sensitivity.

Solution to Problem

The present inventors attempted to change various elements of an immunochromatographic test strip so as to solve the problem. First, following the prior arts, the present inventors tried to improve a conjugate. Specifically, various attempts are made in studies on adjustment of pH at the time of production of conjugates, a type of a blocking agent, and addition of the blocking agent to a conjugate pad. Among these, the blank color development was reduced in some cases; however, detection sensitivity of an analyte decreased at the same time, and the desired performance was not obtained. Conditions for immobilizing an antibody on an insoluble membrane were then studied. As a result of investigating a treatment of an insoluble membrane with a blocking agent, an amount of antibody to be immobilized, and a type and concentration of saccharide coexistent with the antibody, the present inventors surprisingly found that the blank color development can be significantly reduced while maintaining the detection sensitivity by immobilizing the antibody coexist with a specific reductive saccharide in an immunochromatographic test strip including a porous membrane, thereby completing the present invention. Specifically, the present invention has the following configurations.

(1) An immunochromatographic test strip comprising: at least a sample application region, a development region, and a detection region in which an antibody is immobilized, wherein the detection region includes the antibody and one or more saccharides selected from the group consisting of a reductive monosaccharide and a reductive disaccharide.

(2) The immunochromatographic test strip according to (1), comprising:

a sample pad as the sample application region, and a conjugate pad including an anti-analyte antibody labeled with colloidal gold.

(3) The immunochromatographic test strip according to (1) or (2), wherein a specimen applied to the sample application region is plasma or whole blood.

(4) The immunochromatographic test strip according to any one of (1) to (3), wherein the reductive monosaccharide is glucose or fructose, and wherein the reductive disaccharide is maltose.

(5) An immunochromatographic detection kit comprising: the immunochromatographic test strip according to any one of (1) to (4).

(6) An immunochromatographic detection method comprising: using a following test strip:

an immunochromatographic test strip comprising at least a sample application region, a development region, and a detection region in which an antibody is immobilized, wherein the detection region includes the antibody and one or more saccharides selected from the group consisting of a reductive monosaccharide and a reductive disaccharide.

(7) The immunochromatographic detection method according to (6), wherein the test strip comprises a sample pad as the sample application region, and a conjugate pad including an anti-analyte antibody labeled with colloidal gold.

(8) The immunochromatographic detection method according to (6) or (7), wherein a specimen applied to the sample application region is plasma or whole blood.

(9) The immunochromatographic detection method according to any one of (6) to (8), wherein the reductive monosaccharide is glucose or fructose, and wherein the reductive disaccharide is maltose.

(10) A method for producing an immunochromatographic test strip comprising at least steps of:

(a) disposing an antibody application liquid including an anti-analyte antibody, one or more saccharides selected from the group consisting of a reductive monosaccharide and a reductive disaccharide, and a buffer solution to a porous membrane; and (b) drying the porous membrane wherein a pH of the antibody application liquid is 7.0 to 8.0.

(11) The method for producing the immunochromatographic test strip according to (10), wherein the reductive monosaccharide is glucose or fructose, and wherein the reductive disaccharide is maltose.

(12) The method for producing the immunochromatographic test strip according to (10) or (11), wherein a concentration of the saccharide in the buffer solution is 2.5 to 5%.

(13) A method for suppressing blank color development in an immunochromatographic detection method comprising using a following test strip:

an immunochromatographic test strip comprising at least a sample application region, a development region, and a detection region in which an antibody is immobilized, wherein the detection region includes the antibody and one or more saccharides selected from the group consisting of a reductive monosaccharide and a reductive disaccharide.

Advantageous Effects of Invention

According to the present invention, the color development due to a blank reaction (blank color development) can be reduced while detection sensitivity of an analyte is maintained. Therefore, in the case of visual determination, false positives can be avoided to make determination more accurate, and in the case of determination by an optical device, detection sensitivity can be improved.

DESCRIPTION OF EMBODIMENTS (Immunochromatographic Test Strip)

Figure 1:
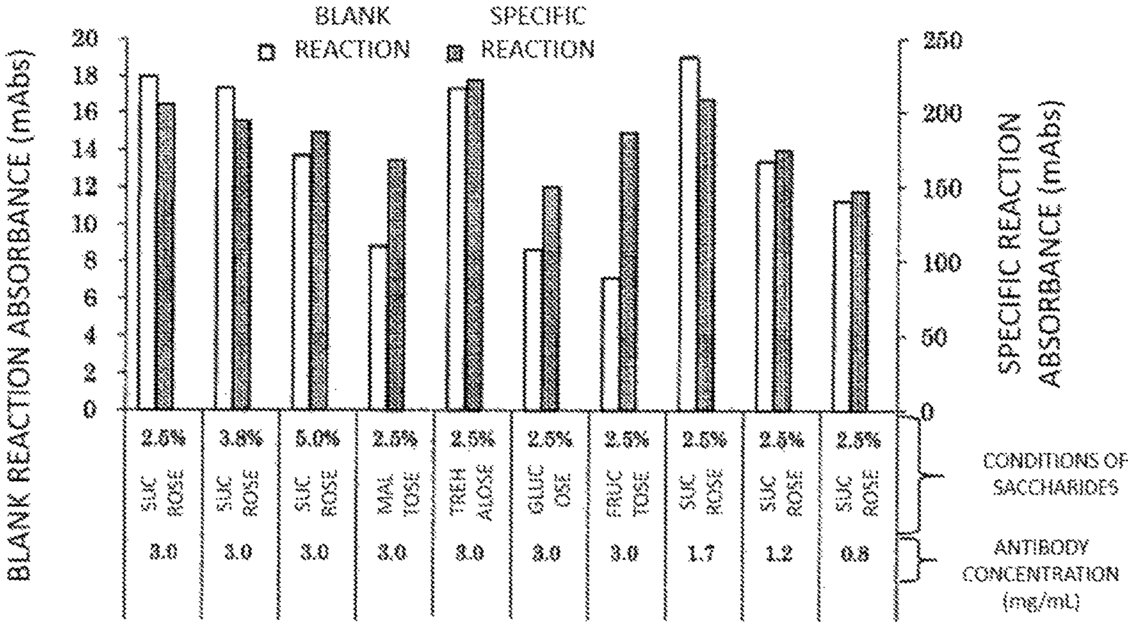
FIG. 1 is a graph showing absorbance of a test line when blank reactions and specific reactions are performed by using various immunochromatographic test strips in which saccharides and concentration of antibody application liquid are changed.

An immunochromatographic test strip of the present invention is an immunochromatographic test strip having at least a sample application region, a development region, and a detection region in which an antibody is immobilized, wherein an antibody for detection is immobilized in a portion of the development region together with specific saccharide to constitute the detection region.

A labeled antibody (also referred to as conjugate) to an analyte is present in presence forms (A to C) described later so that the antibody can pass through the development region after contact with a specimen and reach the detection region.

An example of a test strip embodying these elements is a test strip including a sample pad serving as the sample application region, a conjugate pad holding a labeled antibody to an analyte in a dissolvable state and serving as a portion of the development region, and a porous membrane having a portion on which an antibody for detection is immobilized and serving as the development region and the detection region.

Specifically, a typical test strip for immunochromatography of the present invention has the following configuration:

(1) a sample pad to which a specimen is applicated;

(2) a conjugate pad disposed downstream of the sample pad and holding a conjugate sensitized with a first antibody on a surface of a labeling substance such as colloidal gold in a dissolvable state; and (3) a porous membrane disposed downstream of the conjugate pad and having a detection region in which a second antibody binding to a complex of the conjugate and the analyte is held together with certain saccharide.

The sample pad, the conjugate pad, and the porous membrane may each constitute a separate carrier, or two of them may constitute one carrier, and any form may be available as long as the sample pad, the conjugate pad, and the porous membrane are disposed in this order from upstream to downstream.

In addition to the constituent elements described above, the immunochromatographic test strip may have one or more of absorption pads and 3rd pads further disposed and mounted thereon.

The test strip is usually arranged on a solid phase support such as a plastic adhesive sheet (hereinafter also referred to as a backing sheet).

A polyester film etc., may be laminated on the test strip for the purpose of increasing the mechanical strength of the porous membrane on which the antibody is immobilized and preventing evaporation of moisture (drying) during an assay.

A detection method using the immunochromatographic test strip of the present invention is performed as follows.

When the specimen is dropped onto the sample application region and the specimen includes an analyte, the analyte specifically binds to the labeled antibody to form a complex. The complex is developed in the development region in the downstream direction and binds to the immobilized antibody in the detection region. In the detection region, a sandwich-type complex of the labeled antibody, the analyte, and the immobilized antibody is formed, and therefore, the analyte can qualitatively or quantitatively be analyzed by detecting this complex. Examples of the detection include a method of determining coloration by visual observation and a method of detecting an optical parameter derived from a label by an optical means. When the optical means is used, detection can manually or automatically be performed, and continuous measurement can also be performed.

(Porous Membrane)

The porous membrane used in the immunochromatographic test strip of the present invention has the antibody for detection immobilized on the front surface thereof while the back surface is usually lined with an impermeable film etc. since the membrane is porous.

The porous membrane (hereinafter also simply referred to as a membrane) can be made of any material. Examples thereof include, but not limited to, porous membranes of polyethylene, polyethylene terephthalate, nylons, glass, polysaccharides such as cellulose and cellulose derivatives, or ceramics. Specific examples can include glass fiber filter paper and nitrocellulose membrane commercially available from Merck Millipore, Toyo Roshi Kaisha, GE Healthcare, etc. By appropriately selecting a pore size and a structure of the porous membrane, a flow rate of the immune complex of the colloidal gold-labeled antibody and the analyte flowing through the membrane can be controlled. Since an amount of the labeled antibody binding to the antibody immobilized on the membrane can be adjusted by controlling the flow rate in the membrane, the pore size and the structure of the membrane are desirably optimized in consideration of combination with other constituent materials of the immunochromatographic test strip of the present invention.

(Immobilization of Antibody on Porous Membrane)

The antibody to the analyte of the present invention can be immobilized on the porous membrane by a generally well-known method. For example, in the case of the flow-through type, the antibody is adjusted to a predetermined concentration, and a constant amount of the solution thereof is applied to the porous membrane in a specific symbol shape such as a dot or +. In this case, to ensure the reliability of the immunochromatographic detection method, a protein or compound capable of binding to the conjugate is typically immobilized at a position different from the antibody to the analyte to form a "control detection region". An antibody for control can be immobilized at a position different from the antibody to the analyte to form a "control detection region".

In the case of the lateral-flow type, the antibody is adjusted to a predetermined concentration, and the solution thereof is applied in a line shape to the porous membrane by using an apparatus etc. having a mechanism capable of moving a nozzle in a horizontal direction while discharging the solution at a constant rate therefrom. In this case, the concentration of the antibody is preferably 0.1 to 5 mg/mL, more preferably 0.5 to 3 mg/mL. An amount of the antibody immobilized on the porous membrane can be optimized by adjusting an amount of application dropped onto the porous membrane in the case of the flow-through type, and can be optimized by adjusting a rate of discharge from the nozzle of the apparatus described above in the case of the lateral-flow type. Particularly, in the case of the lateral-flow type, 0.5 to 2 μL/cm is preferable. In the present invention, the term "flow through membrane assay" refers to a method in which a specimen solution etc. are developed to pass perpendicularly through the porous membrane, and the term "lateral flow membrane assay" refers to a method in which a specimen solution etc. are developed to move in a direction parallel to the porous membrane.

In the present invention, regarding the position of application of the antibody to the analyte onto the porous membrane, in the case of the lateral-flow type, the position can be arranged such that the conjugate is developed from the conjugate pad due to the capillarity and sequentially passes through lines to which respective antibodies are applied. Preferably, the line formed by applying the antibody to the analyte is located upstream, and the line formed by applying the control antibody is preferably located downstream thereof. In this case, the lines are desirably spaced at a sufficient distance so that the signal of the label can be detected. Even in the case of the flow-through type, the position of application of the antibody to the object may be arranged so that the signal of the label can be detected.

(Certain Saccharide)

In the present invention, the antibody immobilized on the porous membrane is characterized by coexistence with a certain saccharide. The certain saccharide is a reductive monosaccharide or a reductive disaccharide, examples of the reductive monosaccharide include glucose, fructose, and galactose, and examples of the reductive disaccharide include maltose, lactose, and cellobiose. Among these, glucose, maltose, and fructose are preferable, and fructose is most preferable. It is considered that the coexisting reductive saccharide prevents denaturation due to oxidation of the antibody and prevents non-specific adsorption of a non-specific substance in a sample to the membrane, i.e., a blank reaction. The reason why reductive tri- or higher saccharides are not preferable is that it is difficult to handle because the solubility is low, and that it is impossible to effectively prevent the denaturation of the antibody due to oxidation due to a low ratio of reducing terminals per molecular weight.

A holding amount of the saccharide immobilized on the porous membrane of the present invention may appropriately be set depending on a type of desired analyte and required sensitivity and, for example, the lower limit of the holding amount per length of a test line is preferably 0.01 mg/cm or more, more preferably 0.02 mg/cm or more, and most preferably 0.025 mg/cm. The upper limit is preferably 0.1 mg/cm or less, more preferably 0.07 mg/cm or less, and most preferably 0.05 mg/cm or less.

The preferable range is preferably 0.01 mg/cm to 0.1 mg/cm, more preferably 0.02 mg/cm to 0.07 mg/cm, and most preferably 0.025 mg/cm to 0.05 mg/cm.

A method of allowing the antibody and the saccharide to coexist in the porous membrane may be any method, such as a method of immobilizing the antibody on the porous membrane and then holding the saccharide, or conversely, a method of holding the saccharide in the porous membrane in advance and then immobilizing the antibody, or a method of adding saccharide to an antibody solution and applying the antibody solution including the saccharide to the porous membrane before drying and holding.

Although the reason why the blank reaction is reduced by holding the certain saccharide of the present invention and the antibody for detection in a coexisting manner in the detection region is not clear, it is considered that this plays a role of preventing the conjugate dissolved and developed due to application of the specimen from adsorbing in the detection region on the porous membrane. It is also presumed that since the certain saccharide of the present invention is a monosaccharide or a disaccharide and has excellent solubility and a reducing property, the saccharide is rapidly dissolved to prevent the denaturation due to oxidation of the antibody when the conjugate develops and reaches the detection region, which enables the conjugate to rapidly flow away without clogging so that the blank color development is suppressed.

A method of applying the antibody solution including the certain saccharide of the present invention to the porous membrane will hereinafter be described.

The antibody solution applied to the porous membrane can usually be prepared by using a predetermined buffer solution. Examples of the type of the buffer solution include commonly used buffer solutions such as phosphate buffer solution, Tris buffer solution, and Good's buffer solution, and among these, phosphate buffer solution is desirable. The pH of the buffer solution is preferably in a range of 6.0 to 9.5, more preferably 7.0 to 8.5, and most preferably 7.5 to 8.0. In addition to the specific saccharide of the present invention, the buffer solution may further include salts such as NaCl, preservatives, antiseptics such as ProClin, etc. The salts include those included for adjusting the ionic strength such as NaCl, and those added at the step of adjusting the pH of the buffer solution such as sodium hydroxide. After immobilizing the saccharide and the antibody on the porous membrane, blocking can further be performed by coating an area other than the antibody immobilization site with a normally used blocking agent turned into the form of solution or vapor.

The lower limit of the concentration of the saccharide in the antibody solution is preferably 1.0% or more, more preferably 1.5% or more, further preferably 2.0% or more, and most preferably 2.5% or more. The upper limit is preferably 10.0% or less, more preferably 7.0% or less, further preferably 6.0% or less, and most preferably 5.0% or less. The preferable range is preferably 1.0 to 10.0%, more preferably 1.5% to 7.0%, further preferably 2.0 to 6.0%, and most preferably 2.5 to 5.0%.

In this description, the porous membrane having the antibody immobilized thereon as described above may be referred to as an "antibody-immobilized membrane".

(Sample Pad)

The sample pad used in the present invention is a site serving as the sample application region receiving a sample, and any substances and forms are available as long as those in a state of being molded into a pad can absorb a liquid sample and allow passage of the liquid and the components of the analyte.

The sample pad of the present invention can be pretreated to improve permeability.

When whole blood is measured, an erythrocyte agglutinating agent can be included. In this case, the agent may be included in at least a portion of the sample pad or may be included in the whole thereof.

Specific examples of materials suitable for the sample pad include, but not limited to, glass fiber, acrylic fiber, hydrophilic polyethylene material, dry paper, paper pulp, woven fabric, etc. Preferably, a glass fiber pad is used. The sample pad can also have a function of a conjugate pad described later. The sample pad can also include a blocking reagent usually used as needed without departing from the object of the present invention and without affecting the reaction system.

(Conjugate)

In the conjugate of the present invention, an antibody to an analyte or a control antibody (or an antigen) is conjugated on a label.

The label used in the present invention may be any label capable of constituting the conjugate through sensitization (conjugation) of the antibody and capable of serving as the label in a method in which the label is brought into contact with a sample to detect an object (antigen) in the sample, and examples thereof include colloidal gold particles, colloidal platinum particles, colored latex particles, and magnetic particles, among which colloidal gold and colored latex are desirable, and colloidal gold is more desirable. The particle diameter thereof may be adjusted such that a desired detection sensitivity of a measurement object is obtained depending on each type and, for example, the average particle diameter of the colloidal gold particles is preferably 20 to 100 nm, more preferably 30 to 100 nm, particularly preferably 30 to 70 nm.

In the conjugate of the present invention, it is also possible to block a region on the surface of colloidal gold or the like to which the antibody is not bound with a blocking agent.

Regarding the presence form of the conjugate, the conjugate may be present as the conjugate pad, i.e., in a state of being included in a dedicated pad (conjugate pad) other than the sample pad, the 3rd pad, and the porous membrane (type A), or may be present as a conjugate region in a portion of the sample pad (type B). Alternatively, the conjugate may be present as an individual detection reagent separately from the test strip so as to be mixed with the specimen (type C).

A typical example of the test strip having the conjugate in the presence form of the type A will hereinafter be described.

Figure 3:
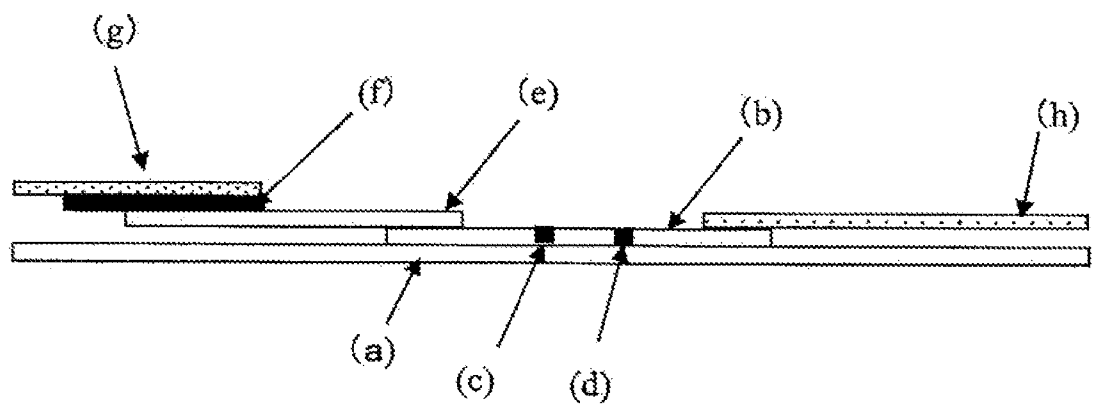
FIG. 3 is a perspective view showing an immunochromatographic test strip of the present invention.

The sample pad, the conjugate pad, the 3rd pad, and the porous membrane are arranged in this order from upstream to downstream in the flow direction of the sample and are arranged such that upper and lower layers at least partially overlap with each other. A test strip of such an arrangement example is shown in FIG. 3.

When a sample including an analyte is applicated to the sample pad of such a test strip, the analyte flows through the sample pad to the conjugate pad on the downstream side. In the conjugate pad, the analyte and the conjugate come into contact with each other and pass through the pad while forming a complex. Subsequently, the complex passes through the 3rd pad disposed in contact with the lower surface of the conjugate pad and is developed into the porous membrane.

Since the antibody that binds to an analyte is immobilized on a portion of the porous membrane, the complex is bound and immobilized onto this membrane. The immobilized complex can visually be detected as a coloration derived from the labeling substance, and can also be detected by a means detecting absorbance, reflected light, fluorescence, magnetism, etc.

The test strip having the conjugate in the presence form of the type B will then be described.

A difference from the type A test strip is that the sample pad and the conjugate pad are integrated, i.e., that the sample application region and the conjugate part are formed in portions of the sample pad.

The sample application region is a section to which the sample including an analyte is applicated, while the conjugate region is a section that includes the conjugate, and the sample application region is located upstream side of the conjugate region.

The test strip having the conjugate in the presence form of the type C will then be described.

The difference from the type A test strip is that the conjugate pad is absent in the test strip and that the conjugate is present as a separate conjugate reagent. For example, a filter chip may be included that has the conjugate incorporated in a filter. By using such a filter chip to filter a specimen with the filter, the conjugate held in the filter and the analyte are combined to form a complex (aggregate). This complex can be applicated to the same test strip as the type A except for the absence of the conjugate pad, so as to detect the analyte.

(Detection Reagent)

In the present invention, the "detection reagent" is specifically a solution including at least a conjugate.

The detection reagent may include, for example, one or more types of stabilizers, solubilizers, etc. for the purpose of maintaining the conjugate in a stable state so as to facilitate the specific reaction of the antibody immobilized on the conjugate with the analyte when mixed with the sample, or to rapidly and effectively dissolve and fluidize the conjugate. Examples of the stabilizers, solubilizers, etc. can include bovine serum albumin (BSA), sucrose, casein, and amino acids.

The detection reagent may also include known sensitizers and chelating agents such as EDTA and EGTA as needed for the purpose of improving the detection sensitivity.

In this description, the term "detection" or "measurement" must be construed in the broadest sense, including the existence proof and/or the quantitation of the analyte and must not be construed in a limited manner in any sense.

(Sample Diluent)

A diluent may be used in the present invention if dilution of a specimen is required depending on concentration of an analyte in the specimen. The diluent having any composition may be used as long as the diluent does not significantly inhibit the antigen-antibody reaction or, conversely, does not significantly facilitate the reaction resulting in excessive aggregation of the label and causing a defect of development by capillarity, and does not make the signal detection of the antigen-antibody reaction depending on antigen concentration impossible.

(Conjugate Pad)

In the present invention, the "conjugate pad" is acquired by drying a material suitable for the conjugate pad described later impregnated with a detection reagent specifically reactive with the analyte. The conjugate pad has a function of allowing the detection reagent and the analyte to form a complex when the sample passes through the conjugate pad. The conjugate pad itself may be disposed in contact with the porous membrane on which the antibody is immobilized. Alternatively, the conjugate pad may be disposed in contact with the sample pad so as to receive a specimen passing through the sample pad as a capillary flow and then transfer the specimen as a capillary flow to the membrane via the 3rd pad in contact with a surface different from the contact surface for the sample pad.

Examples of materials suitable for the conjugate pad include, but not limited to, paper, cellulose mixture, nitrocellulose, polyester, acrylonitrile copolymer, glass fiber, and nonwoven fiber such as rayon. Preferably, a glass fiber pad is used.

The conjugate pad may include a "control reagent" for securing reliability of an immunochromatographic detection method, for example, an antibody labeled with a label and not reactive with a specimen component, and a highly antigenic protein such as KLH (keyhole limpet hemocyanin) labeled with a label, as needed. These control reagents are components (substances) considered as having no possibility of presence in the sample and can appropriately be selected.

(3rd Pad)

In the present invention, the 3rd pad can be disposed between the sample pad and the insoluble membrane for the purpose of removing components unnecessary for detection of the analyte out of reactive components in the specimen and the detection reagent so that components necessary for reaction can smoothly be developed in the porous membrane on which the antibody is immobilized. For example, blood cells and insoluble blood cell fractures are desirably removed as the components unnecessary for detection. The 3rd pad may also be given an additional effect of preliminarily removing aggregates growing to a size preventing the movement to and the smooth development through the antibody-immobilized membrane, among the aggregates generated by the antigen-antibody reaction.

The 3rd pad may be made of any material and in any form allowing the passage of liquid and a component to be detected as well as the detection reagent. Specific examples include, but not limited to, glass fiber, acrylic fiber, hydrophilic polyethylene material, dry paper, paper pulp, fabric, etc. The 3rd pad may be referred to as a blood cell separation membrane when used for the purpose of separating blood cells. In the present invention, when whole blood is used as a specimen, the blood cell separation membrane is desirably used for certainly separating and removing blood cells not completely removed by the sample pad alone.

(Erythrocyte Agglutinating Agent)

In the present invention, when whole blood is used as a specimen, an erythrocyte agglutinating agent or an erythrocyte binding component is desirably used together in addition to the use of the 3rd pad. Although the erythrocyte agglutinating agent or the erythrocyte binding component to be used together is not particularly limited, known examples thereof include lectin, a polyclonal antibody, and a monoclonal antibody, and a polycationic erythrocyte agglutinating agent is also usable. Examples of known polycationic erythrocyte agglutinating agents include polybrene, polylysine, polyacrylic amine, and polyalanine, and polybrene is preferable among them. Polybrene has a chemical name, hexadimethrine bromide, and is one of cationic polymers to which CAS No. 28728-55-4 is assigned.

The erythrocyte agglutinating agent or the erythrocyte binding component can be used in a form in which the agent or the component is added to a diluent for diluting a specimen or directly added to a specimen, or can be included in the sample application region (sample pad) of the immunochromatographic test strip. In such a use form, erythrocytes in whole blood are agglutinated.

(Absorption Pad)

In the present invention, the absorption pad is a portion having liquid absorbability for controlling the development of the specimen by absorbing the specimen that has developed and passed through the porous membrane. In the lateral-flow type, the absorption pad may be disposed on the most downstream side of the test strip, and in the flow-through type, the absorption pad may be disposed on a lower portion of the antibody-immobilized membrane, for example. For the absorption pad, for example, filter paper can be used; however, the present invention is not limited thereto.

(Detection Device)

The immunochromatographic test strip of the present invention can be stored/mounted and used in a suitable container (housing) in consideration of the size of the test strip, the method and position of addition of the specimen, the immobilization position of the antibody on the antibody-immobilized membrane, a signal detection method, etc., and the state of being stored/mounted in this way is referred to as a "device".

(Others)

In this description, the "porous membrane" may be represented as a "solid phase", and physically or chemically supporting an antigen or an antibody with the porous membrane or the supporting state may be represented as "immobilizing", "immobilized", "solid phased", "sensitization", or "adsorption".

(Specimen)

In the detection method of the present invention, the "specimen" including the analyte refers to a biological sample such as blood, urine, sputum, saliva, nasal discharge, nasal cavity swab, throat swab, other body fluids, and feces. The biological sample may directly be used as a specimen, and a sample appropriately diluted with a diluent or extracted and/or filtered is also included in the specimen of the present invention. Examples of blood specimens include whole blood, erythrocytes, plasma, serum, etc.

The blood specimen also includes a specimen collected by a blood collection tube to which an anticoagulant such as EDTA or heparin is added at the time of blood collection.

(Analyte)

The analyte of the present invention is a substance present in a biological specimen such as blood (whole blood), erythrocytes, serum, plasma, urine, saliva, or sputum and examples thereof include: inflammation-related markers such as CRP (C-reactive protein), IgA, IgG, and IgM; coagulation or fibrinolysis markers such as fibrin degradation products (e.g., D-dimer), soluble fibrin, TAT (thrombin-antithrombin complex), and PIC (plasmin-plasmin inhibitor complex); circulation-related markers such as oxidized LDL, BNP (brain natriuretic peptide), H-FABP (cardiac fatty acid-binding protein), cardiac troponin I (cTnI); metabolism-related markers such as adiponectin; tumor markers such as CEA (carcinoembryonic antigen), AFP ($\alpha$-fetoprotein), CA19-9, CA125, and PSA (prostate-specific antigen); infectious disease-related markers such as HBV (hepatitis B virus), HCV (hepatitis C virus), *Chlamydia trachomatis*, and gonococcus; allergen-specific IgE (immunoglobulin E), hormones, and drugs. Among these, D-dimer, CRP, BNP, H-FABP, cTnI, etc. associated with a high desire to use whole blood as a specimen are more preferable.

(Antibody Used in the Present Invention)

The antibody to the analyte used in the present invention is not limited by a method of preparation as long as the antibody specifically reacts with the analyte, and may be a poly clonal antibody or a monoclonal antibody. In general, hybridomas producing the antibody can be prepared by cell fusion between the spleen cells of an animal immunized by using the analyte as an immunogen and the myeloma cells of the same species according to the method of Kohler and Milstein (see Nature, Vol. 256, p.495 (1975)).

The antibody of the present invention can be a whole antibody molecule as well as a functional fragment of an antibody having an antigen-antibody reaction activity and can be an antibody obtained through an immunization step of animals, as well as an antibody obtained by using a gene recombination technique, or a chimera antibody. Examples of the functional fragment of the antibody include $F(ab')_2$ or Fab', and these functional fragments can be produced by treating the antibody obtained as described above with a proteolytic enzyme (e.g., pepsin or papain).

In a relationship between an antibody for immobilization on a label (first antibody) and an antibody for immobilization on a porous membrane (second antibody) when the antibodies used in the measurement method are monoclonal antibodies, the epitope of the second antibody used is different from that of the first antibody when the epitope of the first antibody is monovalent, and the epitope of the second antibody used may be the same as or different from that of the first antibody when the epitope of the first antibody is polyvalent.

(Kit)

A detection kit utilizing the immunochromatographic test strip of the present invention may be a kit that includes an immunochromatographic test strip including at least a sample application region, a development region, and a detection region on which an antibody is immobilized, and the immunochromatographic test strip is characterized in that the detection region includes an antibody together with one or more saccharides selected from the group consisting of a reductive monosaccharide and a reductive disaccharide.

The detection kit may include another reagent required for detection (e.g., a detection reagent including a conjugate), a specimen diluent, a test tube, a cotton swab for feces collection, an instruction manual, a housing for storing the test strip, etc.

Specific examples of the present invention will hereinafter be described; however, these are for illustrative purposes only, and the present invention is not limited thereto.

EXAMPLES

Example 1

The concentration and type of saccharide coexisting with an anti-analyte antibody and the antibody concentration were changed in the detection region to make a comparison in each of blank and specific reactions.

1. Fabrication of Immunochromatographic Detection Device of the Present Invention 1) Preparation of Colloidal Gold-Labeled Anti-cTnI Monoclonal Antibody (Anti-cTnI Antibody Conjugate)

(i) Preparation of Colloidal Gold Solution

To 5000 mL of purified water heated to 93° C., 10 mL of a 7% (w/v) triammonium citrate aqueous solution was added and mixed by stirring. Subsequently, 10 mL of a 5% (w/v) tetrachloroauric(III) acid aqueous solution was added and reacted for 10 minutes with stirring, and the reaction solution was then boiled. Subsequently, the solution was cooled in ice water to prepare a solution of colloidal gold having an average particle diameter of 60 nm. This solution of colloidal gold having an average particle diameter of 60 nm was adjusted with purified water to an absorbance of 1 OD/mL at the maximum absorption wavelength of colloidal gold.

(ii) Preparation of Anti-cTnI Antibody Conjugate

To 200 mL of the 1 OD/mL colloidal gold solution (pH 8.0), 10 mL of an anti-cTnI monoclonal antibody diluted to 20 μg/mL with a 2 mM Tris-hydrochloric acid buffer solution (pH 7.0) was added and stirred for 10 minutes at room temperature. To the mixture liquid of the colloidal gold and the antibody, 10 mL of purified water including 0.5% (w/v) of Neo Protein Saver (NPS, Toyobo, No. NPS-301) was added and stirred for 5 minutes at room temperature. Subsequently, the mixture was centrifuged at 11900×g for 45 minutes at 10° C. After removing supernatant, 10 mL of a 0.2% (w/v) NPS aqueous solution was added to an obtained sediment to suspend a conjugate to obtain an anti-cTnI antibody conjugate.

(iv) Preparation of Colloidal Gold-Labeled KLH (KLH Conjugate) for Control Line

To 200 mL of the 1 OD/mL colloidal gold solution, 10 mL of KLH (manufactured by Sigma) dissolved in a 2 mmol/L phosphate buffer solution to 375 μg/mL was added and stirred for 10 minutes at room temperature. To the mixture liquid of the colloidal gold and KLH, 10 mL of a 10% bovine serum albumin (BSA) aqueous solution was added and stirred for 5 minutes at room temperature. Subsequently, the mixture was centrifuged at 10° C. for 45 minutes, and after removing supernatant, 1 mL of conjugate dilution buffer was added to an obtained sediment to suspend a conjugate to obtain a KLH conjugate.

2) Fabrication of Conjugate Pad

A conjugate solution was prepared by mixing the anti-cTnI antibody conjugate at 3 OD/mL, the KLH conjugate at 0.75 OD/mL, 0.5% LipidureBL-1301, 0.25 mg/ml Hetero-block, 2.4% lactose, 2.0% NPS, 20 mM MOPS (pH 7.2), and a 1/6 amount of Buffer, Conjugate Dilution (Scripps) based on the total amount, and a glass fiber pad (Merck Millipore) having a certain volume is impregnated with a 1.2-fold amount of the solution relative to the volume of the pad. The pad was dried by heating in a dry oven at 70° C. for 45 minutes to obtain a conjugate pad.

3) Fabrication of Anti-cTnI Monoclonal Antibody-Immobilized Membrane

For a test line, a 10 mM phosphate buffer solution (including 0.09% NaN3) (pH 8.0) including the saccharide and antibody at the concentration (final concentration) shown in the figure was prepared.

For a control line, a phosphate buffered saline including a rabbit anti-KLH polyclonal antibody (manufactured by Bethyl) at a final concentration of 2 mg/mL and sucrose at a final concentration of 2.5% was prepared.

At a position inside one end of a short side of a nitrocellulose membrane (Hi-Flow plus HF180, Merck Millipore), the anti-cTnI monoclonal antibody was set to 1 μL/cm and applied in a line shape perpendicular to the longitudinal direction of the test strip (the development direction of the specimen solution) by using the immunochromatographic dispenser “XYZ3050” (BIO DOT) to form the test line. The anti-KLH polyclonal antibody was similarly applied at an interval of about 4 mm from the position of the test line to form the control line. The membrane was dried at 70° C. for 45 minutes in a dry oven to obtain an antibody-immobilized membrane.

4) Fabrication of Sample Pad

A sample pad pretreatment solution was obtained by adjusting 20 mM MOPS (pH 7.2) including 0.5% lactose and 2% polybrene.

A glass fiber pad (Lydall) was cut to an appropriate size, impregnated with a 1.5-fold amount of the sample pad pretreatment solution relative to the volume of the pad, and dried in a dry oven at 70° C. for 45 minutes, and was used as a sample pad.

5) Fabrication of Immunochromatographic Test Strip

The antibody-immobilized porous membrane was affixed to a plastic adhesive sheet (a), application parts are arranged such that the anti-cTnI antibody (c) on the upstream side of development is followed by the anti-KLH antibody (d), and the blood cell separation membrane (3rd pad) (e) was further mounted on the membrane. Subsequently, the conjugate pad (f) fabricated in 2) was arranged and mounted; the sample pad (g) fabricated in 4) was arranged and mounted to overlap the conjugate pad; and the absorption pad (h) was arranged and mounted at an end on the opposite side. By cutting into a structure having the constituent elements overlapped with each other in this way, an immunochromatographic test strip was fabricated. The test strip may be stored in/mounted on a special plastic housing (having a sample addition window part and a detection window part, not shown in FIG. 3) in the form of an immunochromatographic test detection device at the time of an assay. FIG. 3 shows a schematic configuration diagram of the immunochromatographic test strip.

2. Detection or Measurement by Immunochromatography

From the sample application window of the immunochromatographic test device created as described above, 120 μL of a plasma specimen solution including 1000 μg/mL cardiac troponin I (cTnI) was applied to the sample application region, and after 15 minutes, the coloration amount (signal absorbance) of the test line was measured by using the immunochromatographic reader “Rapid Pia” (registered trademark, Sekisui Medical Co., Ltd.).

Figure 2:
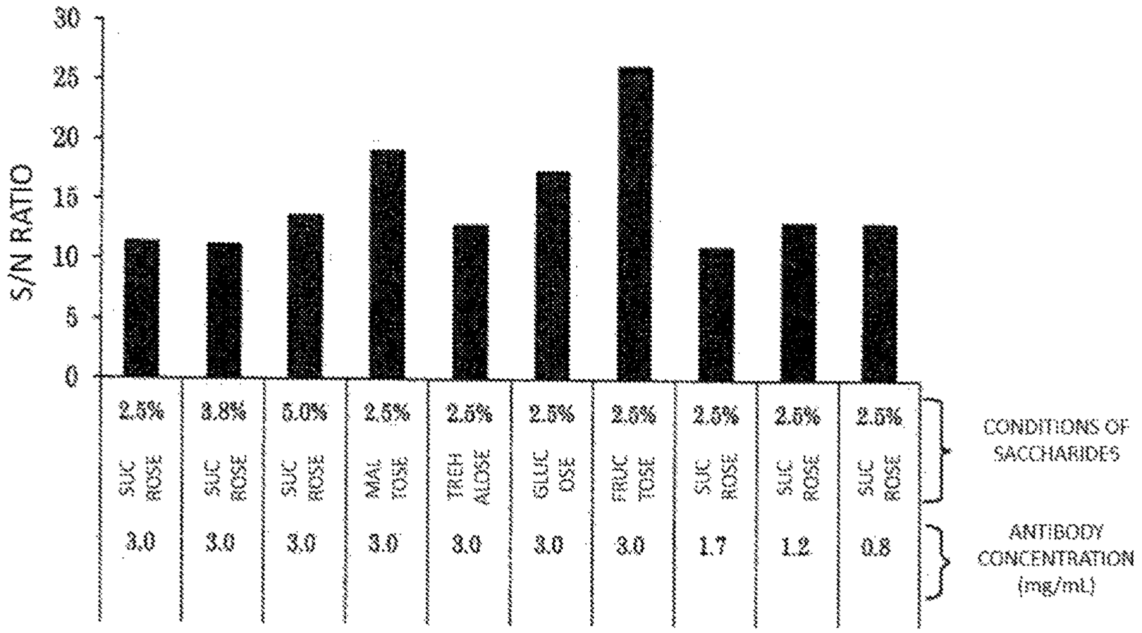
FIG. 2 is a graph showing an S/N ratio of the test results of FIG. 1.

For the plasma specimen solution including no cardiac troponin I (cTnI), the coloration amount (blank absorbance) was measured in the same way. The results are shown in FIG. 1. The results of calculation of the S/N (signal absorbance/blank absorbance) ratio are shown in FIG. 2.

3. Results

By allowing reductive mono- and disaccharides, i.e., fructose, maltose, and glucose, to coexist with the antibody, the blank absorbance value was significantly be decreased while maintaining the measurement sensitivity of the analyte. The S/N ratio was also improved. On the other hand, no improvement was observed by allowing trehalose, which is a nonreducing disaccharide, to coexist with the antibody.

Regarding sucrose, which is also a nonreducing disaccharide and conventionally used, the effect of decreasing the blank value was slight even when the concentration was increased to 3.8% or 5.0%. Although the blank value could be decreased by lowering the antibody concentration from 3.0 mg/mL to 1.7, 1.2, or 0.8 mg/mL, the measurement sensitivity of the analyte also decreased, and no improvement in S/N value was observed.

From the above, it was found that by allowing reductive monosaccharides- and reductive disaccharides to coexist with the antibody for detection, the blank value can be kept low and the S/N ratio can be improved while maintaining a constant sensitivity of the specific reaction with the analyte.

INDUSTRIAL APPLICABILITY

According to the immunochromatographic test strip of the present invention having at least a sample application region, a development region, and a detection region in which an antibody is immobilized, wherein the antibody of the detection region coexists with a certain saccharide, the color development due to the blank reaction can be reduced while maintaining the detection sensitivity of the analyte. Therefore, in the immunochromatographic detection method, a cause of false positives can be eliminated to make an accurate determination in the case of visual determination, and the detection sensitivity can be improved in the case of determination by an optical device.

REFERENCE SIGNS LIST (a) plastic adhesive sheet
(b) antibody-immobilized membrane
(c) anti-cTnI antibody (test line)
(d) anti-KLH antibody (control line)

(e) blood cell separation membrane (3rd pad)
(f) conjugate pad
(g) sample pad
(h) absorption pad

The invention claimed is:

1. An immunochromatographic test strip comprising: at least a sample application region, a development region, and a detection region in which an antibody is immobilized, wherein the detection region includes the antibody and a saccharide selected from the group consisting of a reductive monosaccharide and a reductive disaccharide, wherein the reductive monosaccharide is glucose or fructose, wherein the reductive disaccharide is maltose, and wherein a holding amount of the saccharide immobilized on the detection region is 0.025 mg/cm to 0.05 mg/cm.

2. The immunochromatographic test strip according to claim 1, comprising:

a sample pad as the sample application region, and a conjugate pad including an anti-analyte antibody labeled with colloidal gold.

3. The immunochromatographic test strip according to claim 1, wherein a specimen applied to the sample application region is plasma or whole blood.

4. An immunochromatographic detection kit comprising: the immunochromatographic test strip according to claim 1.

5. An immunochromatographic detection method comprising: using a following test strip:

an immunochromatographic test strip comprising at least a sample application region, a development region, and a detection region in which an antibody is immobilized, wherein the detection region includes the antibody and a saccharide selected from the group consisting of a reductive monosaccharide and a reductive disaccharide, wherein the reductive monosaccharide is glucose or fructose, wherein the reductive disaccharide is maltose, and wherein a holding amount of the saccharide immobilized on the detection region is 0.025 mg/cm to 0.05 mg/cm.

6. The immunochromatographic detection method according to claim 5, wherein the test strip comprises a sample pad as the sample application region, and a conjugate pad including an anti-analyte antibody labeled with colloidal gold.

7. The immunochromatographic detection method according to claim 5, wherein a specimen applied to the sample application region is plasma or whole blood.

8. A method for producing an immunochromatographic test strip comprising at least a sample application region, a development region, and a detection region comprising at least steps of:

(a) disposing an antibody application liquid including an anti-analyte antibody, a saccharide selected from the group consisting of a reductive monosaccharide and a reductive disaccharide, and a buffer solution to a portion of a porous membrane to constitute said detection region, wherein the reductive monosaccharide is glucose or fructose, wherein the reductive disaccharide is maltose, wherein the concentration of the saccharide in the antibody application liquid is 2.5 to 5.0%; and (b) drying the porous membrane to immobilize said anti-analyte antibody in said detection region, wherein a pH of the antibody application liquid is 7.0 to 8.0.

9. An immunochromatographic detection method for detecting an analyte in a sample, said method comprising:

applying a sample to a sample application region in an immunochromatographic test strip comprising at least said sample application region, a development region, and a detection region in which an antibody is immobilized, wherein the detection region includes the antibody and a saccharide selected from the group consisting of a reductive monosaccharide and a reductive disaccharide, wherein the reductive monosaccharide is glucose or fructose, wherein the reductive disaccharide is maltose, and wherein a holding amount of the saccharide immobilized on the detection region is 0.025 mg/cm to 0.05 mg/cm; and detecting said analyte in said detection region.

10. The immunochromatographic detection method according to claim 9, wherein said detection step uses visual detection of coloration derived from the labeling substance, detecting absorbance, detecting reflected light, detecting fluorescence or detecting magnetism.

11. The immunochromatographic detection method according to claim 9, wherein said detection step uses an immunochromatographic reader.

12. The immunochromatographic detection method according to claim 9, wherein said detection step measures absorbance.

13. The immunochromatographic detection method according to claim 9, wherein said detection step involves determining the existence and/or quantitation of the analyte.

* * * * *